United States Patent
Murray, III et al.

(10) Patent No.: US 10,123,895 B2
(45) Date of Patent: Nov. 13, 2018

(54) SINGLE HANDED DEPLOYMENT HANDLE

(71) Applicant: Medtronic, Inc., Minneapolis, MN (US)

(72) Inventors: Robert Murray, III, Santa Rosa, CA (US); Paul Cassidy, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 147 days.

(21) Appl. No.: 14/922,429

(22) Filed: Oct. 26, 2015

(65) Prior Publication Data

US 2016/0038323 A1    Feb. 11, 2016

Related U.S. Application Data

(63) Continuation of application No. 13/219,895, filed on Aug. 29, 2011, now Pat. No. 9,198,788.

(60) Provisional application No. 61/379,146, filed on Sep. 1, 2010.

(51) Int. Cl.
   *A61F 2/966* (2013.01)
   *A61F 2/95* (2013.01)

(52) U.S. Cl.
   CPC ............. *A61F 2/966* (2013.01); *A61F 2/95* (2013.01); *A61F 2002/9517* (2013.01)

(58) Field of Classification Search
   CPC ..... A61F 2/95; A61F 2002/9517; A61F 2/966
   See application file for complete search history.

(56) References Cited

U.S. PATENT DOCUMENTS

| | | |
|---|---|---|
| 7,294,135 B2 | 11/2007 | Stephens et al. |
| 7,419,501 B2 | 9/2008 | Chiu et al. |
| 8,790,386 B2 | 7/2014 | Dwork |
| 9,198,788 B2 * | 12/2015 | Murray, III ............... A61F 2/95 |
| 2003/0074045 A1 | 4/2003 | Buzzard et al. |
| 2003/0167060 A1 | 9/2003 | Buzzard et al. |
| 2005/0060016 A1 | 3/2005 | Wu et al. |
| 2005/0080476 A1 | 4/2005 | Gunderson et al. |
| 2006/0282150 A1 | 12/2006 | Olson et al. |
| 2007/0032860 A1 | 2/2007 | Brooks et al. |
| 2007/0168014 A1 | 7/2007 | Jimenez et al. |
| 2008/0132989 A1 | 6/2008 | Snow et al. |

(Continued)

FOREIGN PATENT DOCUMENTS

| | | |
|---|---|---|
| EP | 1964532 | 9/2008 |
| WO | WO2000/066007 | 11/2000 |

(Continued)

*Primary Examiner* — Katrina Stransky
(74) *Attorney, Agent, or Firm* — Medler Ferro Woodhouse & Mills PLLC (57) ABSTRACT

The present invention is directed to an improved delivery system to deliver and deploy a prosthesis in a body lumen, and methods of use thereof. The improved delivery system allows for operation of the delivery system with one hand while maintaining accuracy in delivery and deployment of the prosthesis. An exemplary embodiment of the delivery system includes a first sheath control on a housing so as to be accessible from the exterior of the housing, wherein the first sheath control is operatively engaged with the sheath and controls movement of the sheath axially proximally with respect to the housing, thereby releasing at least a portion of the prosthesis.

11 Claims, 6 Drawing Sheets

(56) References Cited

U.S. PATENT DOCUMENTS

| | | |
|---|---|---|
| 2008/0188920 A1 | 8/2008 | Moberg et al. |
| 2008/0208209 A1 | 8/2008 | Fischer et al. |
| 2008/0221666 A1 | 9/2008 | Licata et al. |
| 2009/0099650 A1 | 4/2009 | Bolduc et al. |
| 2009/0105801 A1 | 4/2009 | Ivancev |
| 2009/0210046 A1 | 8/2009 | Shumer et al. |
| 2010/0137967 A1 | 6/2010 | Atlani et al. |
| 2012/0078352 A1 | 3/2012 | Wang et al. |

FOREIGN PATENT DOCUMENTS

| | | |
|---|---|---|
| WO | WO2004/060468 | 7/2004 |
| WO | WO2007/046955 | 4/2007 |
| WO | WO2010/005524 | 1/2010 |

\* cited by examiner

SINGLE HANDED DEPLOYMENT HANDLE

RELATED APPLICATION DATA

This application is a Continuation of and claims priority to U.S. patent application Ser. No. 13/219,895, filed Aug. 29, 2011, now allowed, which claims priority to U.S. Provisional Patent Application No. 61/379,146, filed Sep. 1, 2010.

BACKGROUND OF THE INVENTION

Field of the Invention

Exemplary embodiments of the present invention relate to systems and methods for delivering a prosthesis to a desired location in the body. More particularly, the present invention relates to a delivery system for deploying a prosthesis within a body lumen and to methods of delivering a prosthesis to a desired location in a body. The delivery system can be operated with one hand while maintaining accuracy and providing mechanical advantage in deployment of a prosthesis in a body lumen.

Background

Vascular aneurysms are the result of abnormal dilation of a blood vessel, usually resulting from disease and/or genetic predisposition that weakened the arterial wall and allowed it to expand. While aneurysms could occur in any blood vessel, most occur in the aorta and peripheral arteries, with the majority of aortic aneurysms occurring in the abdominal aorta, usually beginning below the renal arteries and often extending into one or both of the iliac arteries.

Aortic aneurysms were commonly treated in open surgical procedures where the diseased vessel segment was bypassed and repaired with an artificial vascular graft. While considered to be an effective surgical technique, particularly considering the alternative of a fatal ruptured abdominal aortic aneurysm, conventional vascular graft surgery suffered from a number of disadvantages. The surgical procedure was complex and required experienced surgeons and well-equipped surgical facilities. Even with the best surgeons and equipment, however, patients frequently were elderly and weakened from cardiovascular and other diseases, reducing the number of eligible patients.

Even for eligible patients prior to rupture, conventional aneurysm repair had a relatively high mortality rate, usually from 2% to 10%. Morbidity related to the conventional surgery included myocardial infarction, renal failure, impotence, paralysis, and other conditions. Additionally, even with successful surgery, recovery took several weeks, and often required a lengthy hospital stay.

In order to overcome some or all of these drawbacks, endovascular prosthesis placement for the treatment of aneurysms has been used. Although promising, many of the proposed methods and apparatuses suffered from undesirable limitations. In particular, accurate delivery and placement of the endovascular prosthesis within the vasculature was problematic.

Stent-grafts (endovascular prostheses) are resilient structures, usually biased to expand against a surrounding luminal wall. Such resiliently-expanding stent-grafts may be tightly compressed within a catheter for delivery, imposing significant radial expansion forces against the surrounding catheter sheath. This may lead to high levels of friction between the stent-graft and the sheath, particularly if the resiliently-expanding structure becomes partially embedded in the sheath material. Thus, a delivery system must be capable of imparting a significant, yet controlled, force to retract the sheath and deploy the stent-grafts.

U.S. Pat. No. 7,419,501 to Chiu et al., which is incorporated herein by reference in its entirety, discloses a delivery system that attempts to address these issues by providing a delivery system having a handle that allows for accurate placement of a stent-graft in a body lumen. The delivery system includes a sheath and a handle. The handle includes: a slide shaft having a threaded outer surface; and a hub assembly coupled to the sheath. The hub assembly includes: an inner slider having a thread tooth pivot support; a thread tooth pivotably mounted to the thread tooth pivot support; and a sleeve having a thread tooth press member pressing on the thread tooth, where motion of the sleeve relative to the inner slider pivots the thread tooth on the thread tooth pivot support to engage and disengage the hub assembly with the threaded outer surface.

U.S. application Ser. No. 13/106,110, filed May 12, 2011, which is incorporated herein by reference in its entirety, discloses a delivery system having an improved handle that allows for operation of the delivery system with one hand while maintaining accuracy in delivery and deployment of a prosthesis in a body lumen. The delivery system includes a sheath and a handle. The handle includes: a slide shaft having a threaded outer surface; and a hub assembly coupled to the sheath. The hub assembly includes: an inner slider having a thread tooth pivot support; a thread tooth pivotably mounted to the thread tooth pivot support; a distal sleeve having a thread tooth press member pressing on the thread tooth; and a proximal sleeve. Motion of the distal sleeve relative to the inner slider pivots the thread tooth on the thread tooth pivot support to engage and disengage the hub assembly with the threaded outer surface. The distal sleeve is rotatably coupled to the proximal sleeve, and the proximal sleeve is prevented from rotating in order to provide a stable grip to allow operation of the catheter with one hand.

BRIEF SUMMARY OF THE INVENTION

Some embodiments of the present invention provide improved delivery systems that allow for operation of the delivery system with one hand while maintaining accuracy in delivery and deployment of a prosthesis in a body lumen.

Some embodiments of the present invention also provide methods of using an improved delivery system that allows for operation of the delivery system with one hand while maintaining accuracy in delivery and deployment of a prosthesis in a body lumen.

Additional features of the invention will be set forth in the description that follows, and in part will be apparent from the description, or may be learned by practice of the invention Some embodiments of the present invention provide a delivery system for delivering a prosthesis to a location in a body, the delivery system including a housing having a longitudinal axis and a distal end hole, a sheath extending from within the housing through and outwardly beyond the distal end hole, wherein the sheath contains the prosthesis at a distal end thereof, a first sheath control disposed on the housing so as to be accessible from the exterior of the housing, wherein the first sheath control is operatively engaged with the sheath, a stop disposed within the housing, the stop being engagable and disengagable with respect to the sheath and configured to, when engaged, confine axial motion of the sheath with respect to the housing within set parameters, and a stop control accessible from the exterior of the housing and operatively connected to the stop, wherein actuation of the stop control causes the stop to disengage or engage with respect to the sheath, wherein a first actuation of the first sheath control causes the sheath to move axially proximally with respect to the housing, thereby releasing at least a portion of the prosthesis.

Some embodiments of the present invention also provide a method of delivering a prosthesis to a desired location in a body, the method including introducing a sheath of a delivery system into a patient's vasculature, wherein a distal tip of the sheath contains the prosthesis, advancing the distal tip of the sheath to the desired location in the body, actuating, in a first direction, a sheath control of the delivery system to cause the sheath to move axially proximally with respect to the housing until further motion of the sheath is prevented by a stop, thereby releasing at least a portion of the prosthesis, actuating a stop control to disengage the stop, and continuing to actuate the sheath control in the first direction until the prosthesis is fully released, wherein the sheath control is disposed on a housing of the delivery system so as to be accessible from the exterior of the housing, and wherein the sheath control is operatively engaged with the sheath, and wherein the stop control is disposed on the housing of the delivery system so as to be accessible from the exterior of the housing, and wherein actuation of the stop control causes the stop to disengage or engage with respect to the sheath.

Both the foregoing general description and the following detailed description are exemplary and explanatory and are intended to provide further explanation of the invention as claimed.

BRIEF DESCRIPTION OF THE FIGURES

The accompanying figures, which are incorporated herein, form part of the specification and illustrate embodiments of prosthetic delivery systems and methods of delivering a prosthesis to a desired location in a body. Together with the description, the figures further serve to explain the principles of and to enable a person skilled in the relevant art(s) to make and use the delivery systems and methods described herein. In the drawings like reference characters indicate identical or functionally similar elements.

DETAILED DESCRIPTION OF THE INVENTION

The following detailed description of prosthetic delivery systems and methods of delivering a prosthesis to a desired location in a body refers to the accompanying figures that illustrate exemplary embodiments. Other embodiments are possible and may fall within the scope of the present invention. Modifications can be made to the exemplary embodiments described herein without departing from the spirit and scope of the present invention. Therefore, the following detailed description is not meant to be limiting.

Further, it would be apparent to one of skill in the art that the systems and methods described below can be implemented in many different embodiments of hardware. Any actual hardware described is not meant to be limiting. The operation and behavior of the systems and methods presented are described with the understanding that various modifications and variations of the exemplary embodiments may be within the scope of the present invention.

Figure 1:
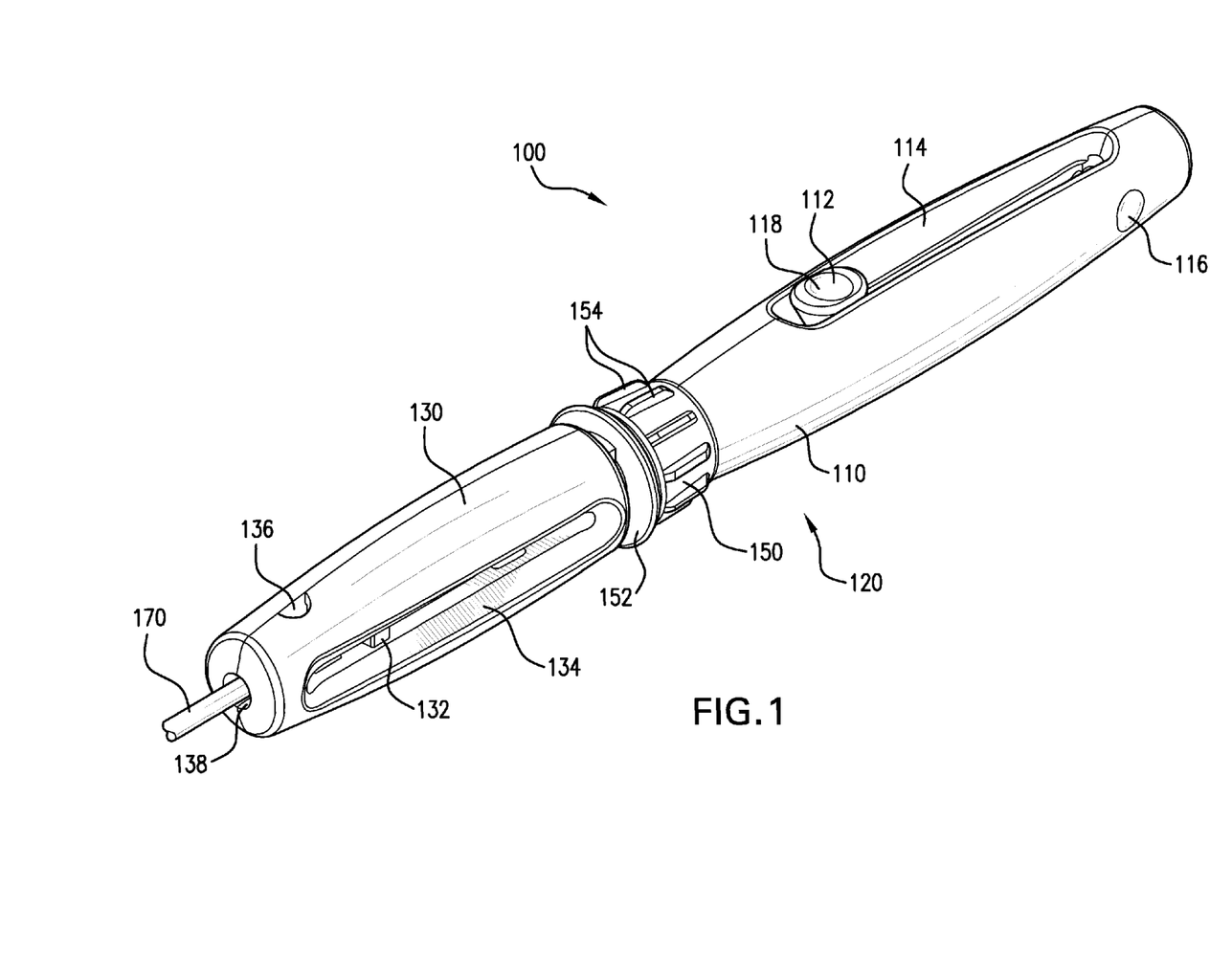
FIG. 1 is a perspective view of a delivery system according to an exemplary embodiment of the present invention.
Figure 2:
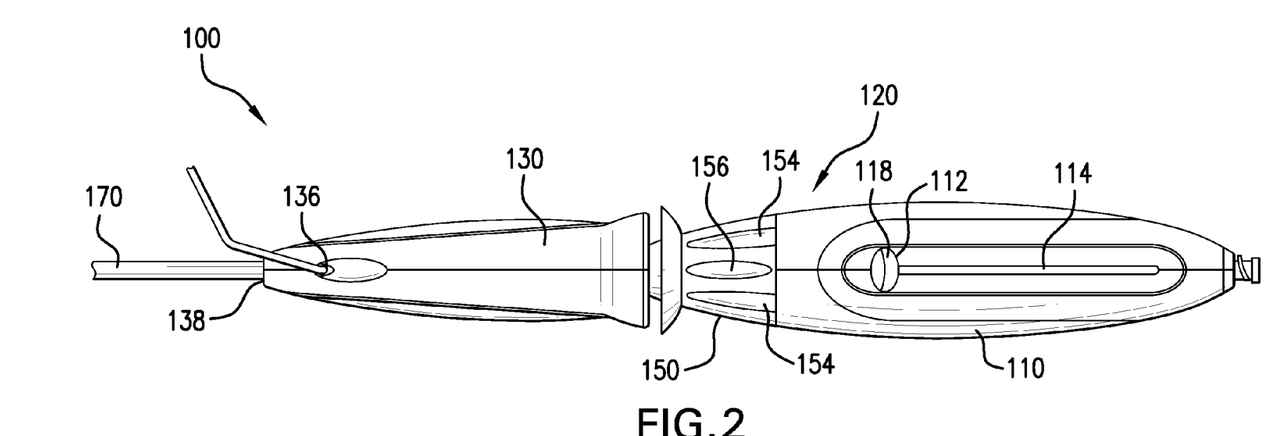
FIG. 2 is a top view of a delivery system according to an exemplary embodiment of the present invention.
Figure 3:
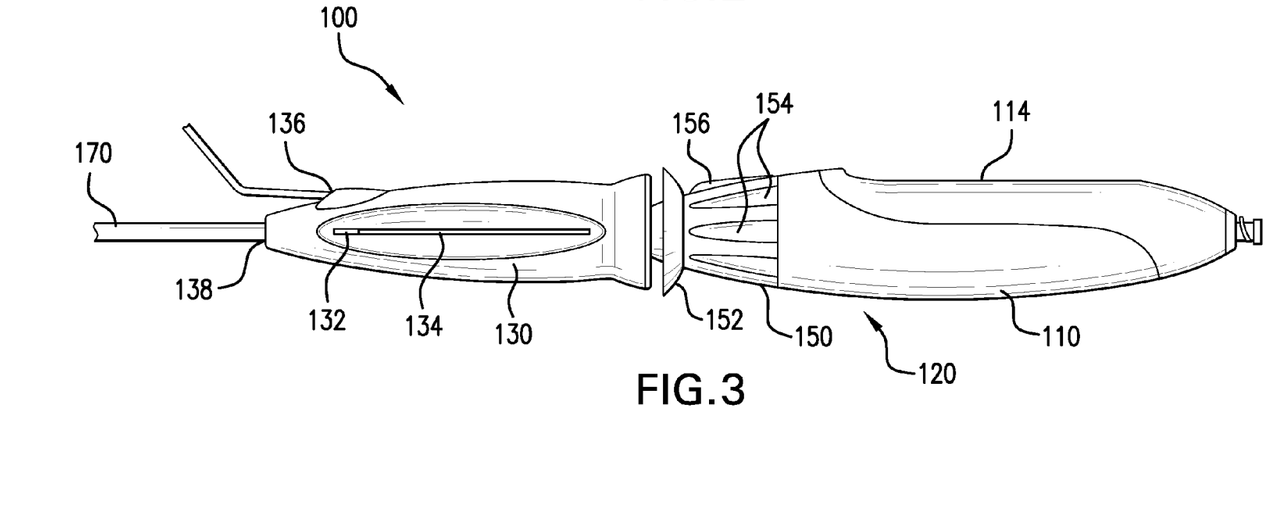
FIG. 3 is a side view of a delivery system according to an exemplary embodiment of the present invention.

FIG. 1 is a perspective view of a delivery system 100 according to an exemplary embodiment of the present invention. FIG. 2 is a top view of an exemplary embodiment of delivery system 100. FIG. 3 is a side view of an exemplary embodiment of delivery system 100. Delivery system 100 includes a housing 120, a first sheath control 150, a stop control 152, and a sheath 170. Housing 120 can include proximal portion 110 (sometimes referred to as a "handle" or "grip") and distal portion 130. Distal portion 130 can include a distal end hole 138.

A distal tip of sheath 170 can releasably contain a prosthesis (not shown). A user can operate delivery system 100 by inserting sheath 170 containing the prosthesis in its distal tip into a body lumen of a patient. The user can then position the distal tip of sheath 170 within the patient's body lumen in a desired location. The user can then operate delivery system 100 to withdraw sheath 170, thereby releasing the prosthesis at the desired location in the patient's body lumen.

Sheath 170 extends from within housing 120 through and outwardly beyond distal end hole 138. Sheath 170 can removably contain a prosthesis (not shown) within its distal end. The prosthesis can be held in position by a prosthesis retainer (not shown) mounted to a delivery shaft (not shown) connected to housing 120.

U.S. application Ser. No. 13/106,110, filed May 12, 2011, which is hereby incorporated by reference in its entirety, discloses systems and methods of controlling motion of a sheath with respect to a housing. As one skilled in the art would appreciate, similar systems and methods can be used in conjunction with the present invention. The present invention, however, is not limited to such use.

First sheath control 150 is mounted to housing 120 so as to be accessible and operable from the exterior of housing 120. First sheath control 150 can be selectively engaged and disengaged with sheath 170. When engaged, first sheath control 150 can be operated to move sheath 170 axially with respect to housing 120. When first sheath control 150 is operated to move sheath 170 proximally with respect to housing 120, sheath 170 can gradually release the prosthesis from its distal end, because the prosthesis will be held axially stationary with respect to housing 120 by the prosthesis retainer and/or delivery shaft. If the prosthesis is only partially released, first sheath control 150 can be operated to move sheath 170 distally with respect to housing 120, thereby recapturing the prosthesis within the distal end of sheath 170.

First sheath control 150 can operatively engage with sheath 170 in a variety of ways that would be apparent to one of skill in the art. For example, first sheath control 150 can include interior threads or other engagement members that align with exterior threads or other engagement members on sheath 170 such that rotation of first sheath control 150 causes axial translation of sheath 170 with respect to housing 120, or sheath 170 can be fixed to a slide shaft that engages first sheath control 150 to cause axial translation of sheath 170 in response to operation of first sheath control 150. Preferably first sheath control 150 can engage with sheath 170 so as to provide mechanical advantage and precise control to a user of sheath control 150 in order to facilitate release or recapture of the prosthesis.

In an exemplary embodiment, first sheath control 150 includes a wheel-shaped control member aligned coaxially with housing 120 and rotatable thereabout. First sheath control 150 can be positioned between proximal portion 110 and distal portion 130 so as to be easily accessible to a user of delivery system 100. First sheath control 150 can cover a portion of housing 120 where proximal portion 110 and distal portion 130 meet, or first sheath control 150 can itself form a part of housing 120 by itself joining proximal portion 110 and distal portion 130. A user will typically grasp proximal portion 110 in one hand such that the forefinger and thumb of the user are positioned proximate to first sheath control 150. Because of the location of first sheath control 150 relative to proximal portion 110 (i.e., grip), as well as the mechanical advantage and precision control provided by first sheath control 150, the user can operate first sheath control 150 to release or recapture the prosthesis with the forefinger and thumb of the user's hand while grasping proximal portion 110 with the remaining fingers and the palm, without the need to employ the user's other hand. First sheath control 150 can be configured such that it does not travel in an axial direction with respect to housing 120.

Delivery system 100 can also include a sheath stop that, when engaged, limits the axial motion of sheath 170 with respect to housing 120. The sheath stop can be configured to allow axial motion of sheath 170 to release only a portion of the prosthesis. Such a feature can provide an indication of how much of the prosthesis has been released, or indicate the point after which recapture of the prosthesis cannot effectively take place. Stop control 152 (sometimes referred to as "stop release" or "⅔ stop release") can be actuated to disengage the sheath stop, thereby allowing axial motion of sheath 170 beyond the limits imposed when the sheath stop is engaged (e.g., allowing axial motion of sheath 170 to its full proximal position). Typically a user would operate stop control 152 to release the sheath stop once the user is certain of proper placement of the prosthesis. Thereafter, the user can operate first sheath control 150 to further and fully release the prosthesis. As shown in FIG. 1, in an exemplary embodiment stop control 152 is a ring located at the distal end of first sheath control 150. To actuate stop control 152 and thereby disengage the sheath stop, a user applies pressure to stop control 152 in a distal direction.

First sheath control 150 can include gripping enhancements 154 on its surface to assist a user in turning first sheath control 150. FIGS. 1-3 depicts ridges extending longitudinally and disposed around the exterior of the wheel of first sheath control 150. Other gripping enhancements can also be used. For example, raised bumps, circular ridges, surface texture, or indents can be disposed on a surface of first sheath control 150. Such gripping enhancements decrease the likelihood that a user's fingers will slip while operating first sheath control 150, and increase the ease with which the user can operate first sheath control 150.

Additionally, first sheath control 150 can include a control indicator 156. Control indicator 156 also can enhance a user's grip on first sheath control 150, however it is shaped differently from gripping enhancements 154. The different shape of control indicator 156 provides tactile feedback to a user operating first sheath control 150, and can thereby indicate to the user the degree to which the first sheath control 150 has rotated.

In some situations, it may be desirable to have more direct control over the movement of sheath 170 than may be provided by first sheath control 150. In an exemplary embodiment, housing 120 includes a second sheath control 112 (also referred to as a "proximal indicator") accessible through a proximal slot 114 extending longitudinally along and through a portion of proximal portion 110. Second sheath control 112 can be fixed to sheath 170 and axially slidable with respect to housing 120. Second sheath control 112 moves within slot 114 during operation of first sheath control 150 as a consequence of first sheath control 150 moving sheath 170. Because second sheath control 112 is accessible through slot 114, it can be viewed by a user, thereby providing to the user an indication of the extent of movement of sheath 170. As an alternative to moving sheath 170 using first sheath control 150, a user can choose instead to move sheath 170 using second sheath control 112. As the user grips proximal portion 110, the user can position his or her thumb (or other portion of his or her hand) on second sheath control 112 and slide second sheath control 112 proximally or distally within proximal slot 114, thereby causing a corresponding movement of sheath 170. Such use of second sheath control 112 to control sheath 170 may be desirable to a user for a variety of reasons. For example, the user can withdraw sheath 170 more quickly with second sheath control 112 than operation of first sheath control 150 would allow.

Depending on the configuration of first sheath control 150, a user's control of the movement of sheath 170 by way of second sheath control 112 may be inhibited by the engagement of first sheath control 150 with sheath 170. To alleviate this difficulty, an exemplary embodiment of the present invention includes a sheath engagement control 118, operable to disengage or engage first sheath control 150 with sheath 170. As shown in FIG. 1, in an exemplary embodiment sheath engagement control 118 coexists with second sheath control 112. This configuration allows a user to apply pressure to sheath engagement control 118 (e.g., by pressing down on sheath engagement control 118 with his or her thumb) to disengage first sheath control 150 from sheath 170, at which point the user can slide second sheath control 112 so as to control movement of sheath 170. The user can release the pressure applied to sheath engagement control 118 in order to re-engage first sheath control 150 with sheath 170. In some exemplary embodiments, sheath engagement control 118 need not be held down to keep first sheath control 150 disengaged with sheath 170, but need only be pressed once to disengage, and once again to re-engage.

Housing 120 can optionally include a proximal flush port 116 in proximal portion 110, and/or a distal flush port 136 in distal portion 130. Proximal flush port 116 and distal flush port 136 can be used to flush cavities within sheath 170 with fluid in order to prevent introducing air into a patient during delivery of the prosthesis.

Distal portion 130 can include a distal slot 134 extending longitudinally along and through distal portion 130. A distal indicator 132 may be viewable to a user through distal slot 134. Distal indicator 132 is connected to sheath 170 and slidable within distal portion 130 along with motion of sheath 170. As such, distal indicator 132 can indicate to a user the extent to which sheath 170 has moved in response to the user's operation of either first sheath control 150 or second sheath control 112.

Figure 4:
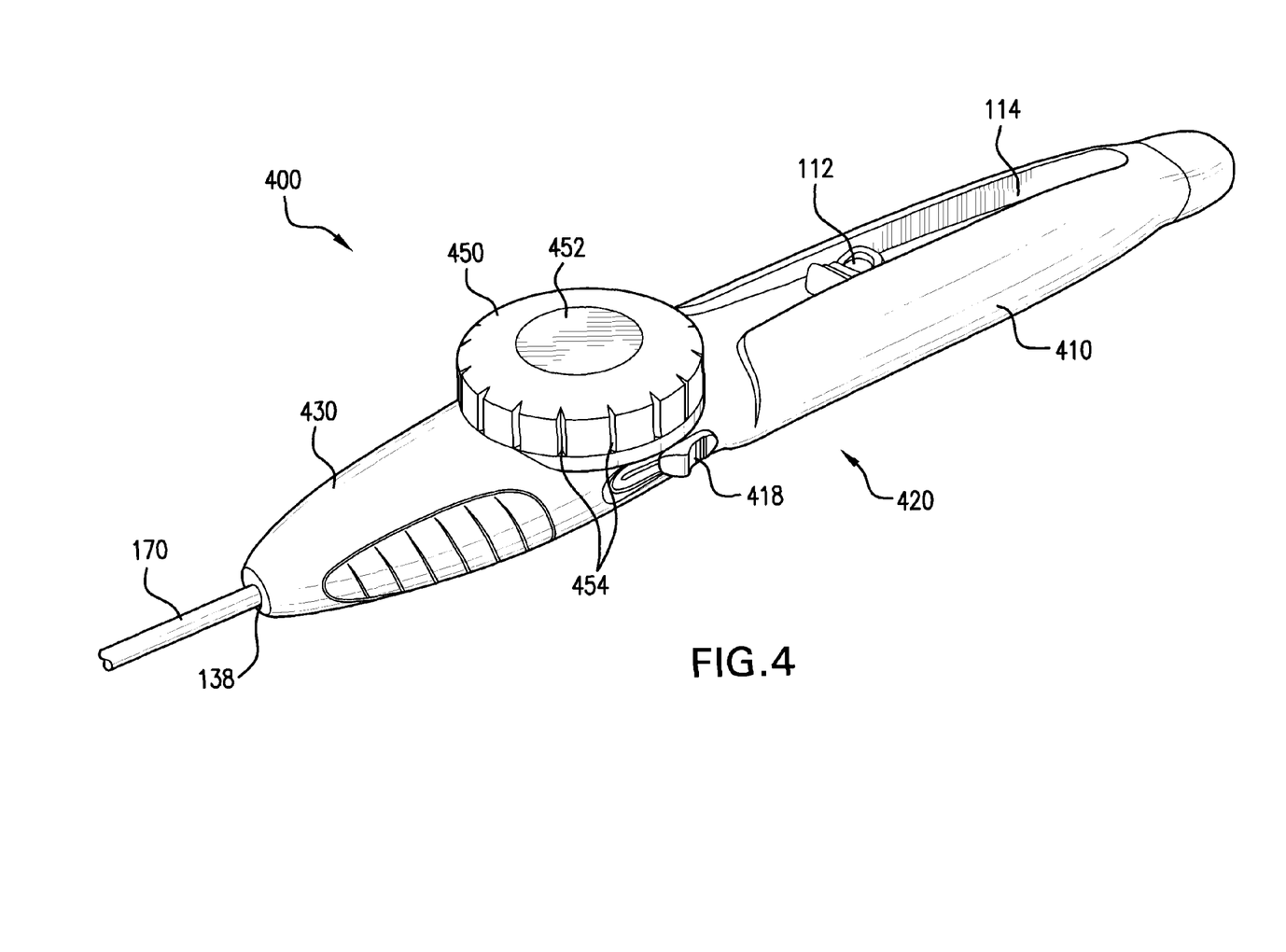
FIG. 4 is a perspective view of a delivery system according to an exemplary embodiment of the present invention.

FIG. 4 is a perspective view of a delivery system 400 according to an exemplary embodiment of the present invention. Description of elements of the exemplary embodiment depicted in FIG. 4 that are the same or operate similarly as those described above with reference to FIGS. 1-3 may be omitted or abbreviated.

In an exemplary embodiment of the present invention, a delivery system 400 includes a first sheath control 450 that includes a wheel-shaped control member rotatably mounted to a housing 420 (housing 420 including a proximal portion 410 and a distal portion 430). First sheath control 450 can be positioned on housing 420 so as to be easily accessible to a user of delivery system 400. A user will typically grasp proximal portion 410 (i.e., grip) in one hand such that the forefinger and thumb of the user are positioned proximate to first sheath control 450. Because of the location of first sheath control 450 relative to proximal portion 410, as well as the mechanical advantage and precision control provided by first sheath control 450, the user can operate first sheath control 450 to release or recapture the prosthesis with the forefinger and/or thumb of the user's hand that is grasping proximal portion 410, without the need to employ the user's other hand. In order to facilitate such operation, first sheath control 450 can be provided with grip enhancers 454, which, in the embodiment of FIG. 4, are grooves extending around the circumference of first sheath control 450 in an axial direction with respect to first sheath control 450.

Delivery system 400 can also include a sheath stop that, when engaged, limits the axial motion of sheath 170 with respect to housing 420. A stop control 452 can be actuated to disengage the sheath stop, thereby allowing axial motion of sheath 170 beyond the limits imposed when the sheath stop is engaged (e.g., allowing axial motion of sheath 170 to its full proximal position). Typically a user would operate stop control 452 to release the sheath stop once the user is certain of proper placement of the prosthesis. Thereafter, the user can operate first sheath control 450 to further and fully release the prosthesis. As shown in FIG. 4, in an exemplary embodiment stop control 452 is a button located in the center of first sheath control 450. To actuate stop control 452 and thereby disengage the sheath stop, a user applies pressure to stop control 452.

Delivery system 400 can also include a sheath engagement control 418 that is separate from second sheath control 112 and is slidably disposed on the exterior surface of housing 420. Sheath engagement control 418 is located proximate to first sheath control 450 so as to allow for single-handed access by a user. Sheath engagement control 418 is slidable in an axial direction with respect to housing 420 between a proximal position and a distal position. Sliding sheath engagement control 418 from one position to the other disengages or engages first sheath control 450 with sheath 170. For example, sliding sheath engagement control from the proximal position to the distal position can cause sheath engagement control 418 to disengage first sheath control 450 with sheath 170, at which point a user can slide second sheath control 112 so as to control movement of sheath 170. The user can slide sheath engagement control 418 from the distal position to the proximal position in order to re-engage first sheath control 450 with sheath 170. In some exemplary embodiments, sheath engagement control 418 is spring-loaded such that it resists sliding from the proximal position to the distal position. In such an exemplary embodiment, a user who has slid sheath engagement control 418 to a distal position in order to disengage first sheath control 450 with sheath 170 need only release sheath engagement control 418 in order to allow sheath engagement control 418 to return to the proximal position and re-engage first sheath control 450 with sheath 170.

Figure 5:
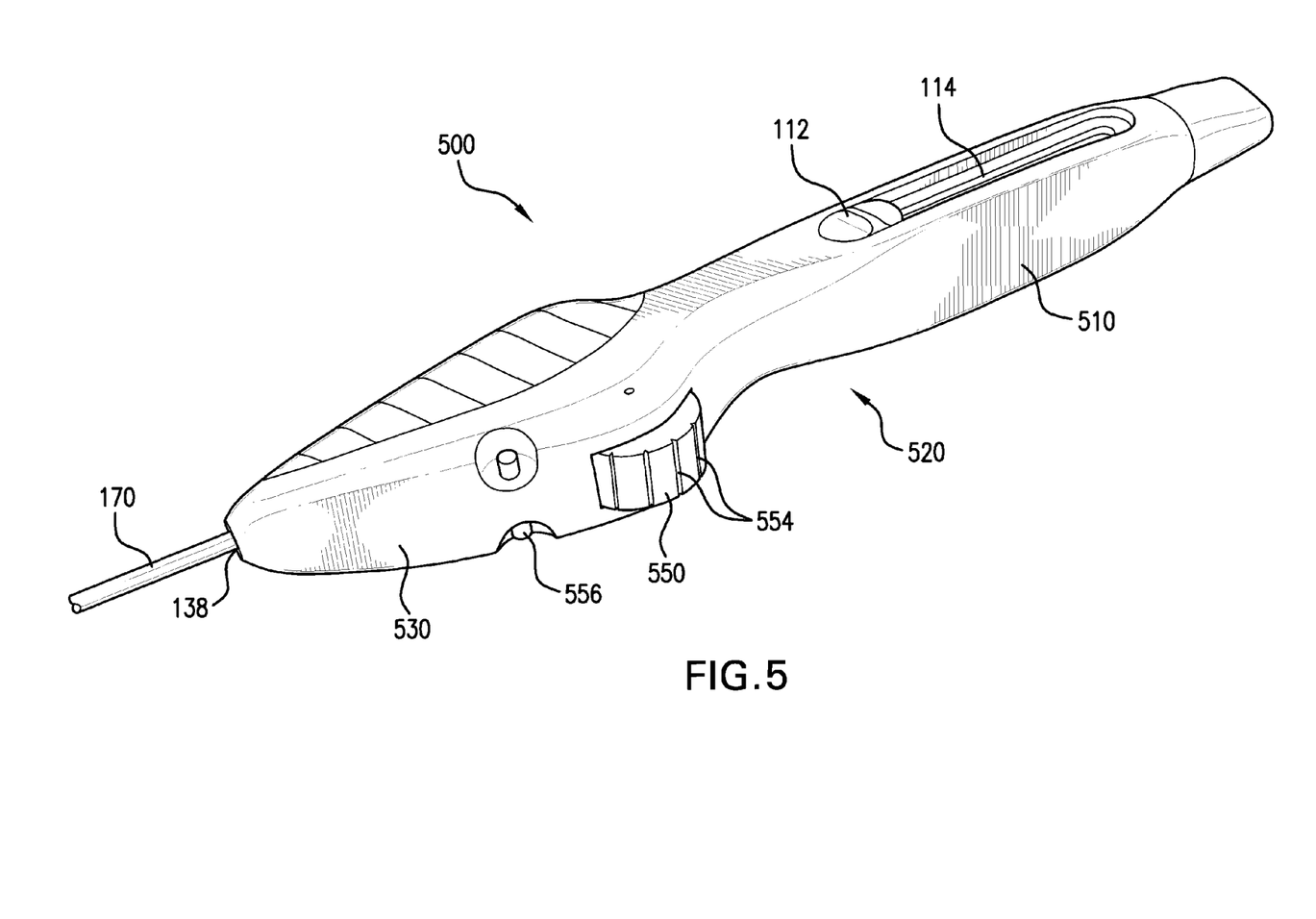
FIG. 5 is a perspective view of a delivery system according to an exemplary embodiment of the present invention.

FIG. 5 is a perspective view of a delivery system 500 according to an exemplary embodiment of the present invention. Description of elements of the exemplary embodiment depicted in FIG. 5 that are the same or operate similarly as those described above may be omitted or abbreviated.

In the embodiment shown in FIG. 5, a delivery system 500 includes a first sheath control 550 that includes a wheel-shaped control member rotatably mounted to a housing 520 (housing 520 including a proximal portion 510 and a distal portion 530) such that the axis of the wheel is offset from the longitudinal axis of housing 520. First sheath control 550 can be partially recessed within housing 520 such that a portion of the exterior surface of first sheath control 550 extends through the surface of housing 520 so as to be accessible from the exterior of housing 520. A user can operate first sheath control 520 by rotating the portion of first sheath control 520 that extends outside housing 520. A user will typically grasp proximal portion 510 in one hand such that the thumb of the user is positioned proximate to first sheath control 550. Because of the location of first sheath control 550 relative to proximal portion 510 (i.e., grip), as well as the mechanical advantage and precision control provided by first sheath control 550, the user can operate first sheath control 550 to release or recapture the prosthesis with the thumb of the user's hand that is grasping proximal portion 510, without the need to employ the user's other hand. In order to facilitate such operation, first sheath control 550 can be provided with grip enhancers 554, which, in the exemplary embodiment of FIG. 5, are grooves extending around the circumference of first sheath control 550 in an axial direction with respect to first sheath control 550.

Delivery system 500 can also include a combination stop control and sheath engagement control 556. Combination stop control and sheath engagement control 556 can be a three-position switch, with a middle position, a left position, and a right position. Combination stop control and sheath engagement control 556 can be a cylindrical element extending through a portion of housing 520 so as to protrude from opposing sides of housing 520, where a user can operate combination stop control and sheath engagement control 556 by pressing on either end. Combination stop control and sheath engagement control 556 is not limited to a cylindrical element. For example, combination stop control and sheath engagement control 556 can be rectangular, triangular, or hexagonal.

Combination stop control and sheath engagement control 556 is shown in FIG. 5 in the middle position. When in the middle position, pressing on a right side of combination stop control and sheath engagement control 556 will cause combination stop control and sheath engagement control 556 to slide from the middle position to the left position, and pressing on the left side of combination stop control and sheath engagement control 556 will cause combination stop control and sheath engagement control 556 to slide from the middle position to the right position. When in the left position, pressing on a left side of combination stop control and sheath engagement control 556 will cause combination stop control and sheath engagement control 556 to slide from the left position to either the middle position or the right position, depending on how far combination stop control and sheath engagement control 556 is pressed. When in the right position, pressing on a right side of combination stop control and sheath engagement control 556 will cause combination stop control and sheath engagement control 556 to slide from the right position to either the middle position or the left position, depending on how far combination stop control and sheath engagement control 556 is pressed.

Of the three potential positions for combination stop control and sheath engagement control 556, one will be a first position in which first sheath control 550 is engaged with sheath 170 and a sheath stop is engaged. Another will be a second position in which first sheath control 550 is disengaged with sheath 170 and the sheath stop is engaged. Another will be a third position in which first sheath control 550 is engaged with sheath 170 and the sheath stop is disengaged. As will be appreciated by one of skill in the art, more or fewer than three positions are possible for combination stop control and sheath engagement control 156, and combinations of first sheath control 550 and sheath stop states other than those described are possible.

In some exemplary embodiments, combination stop control and sheath engagement control 556 can be spring-loaded so as to naturally tend to remain in a neutral position. The neutral position can correspond to the middle position. In such an exemplary embodiment, the portions of combination stop control and sheath engagement control 556 that extend on either side of housing 520 can each correspond independently to one of a stop control and a sheath engagement control. For example, a user can depress and release the left side of combination stop control and sheath engagement control 556 in order to engage or disengage the sheath stop, regardless of the state of engagement of the first sheath control 550 with the sheath 170. Correspondingly, the user can depress and release the right side of combination stop control and sheath engagement control 556 in order to engage or disengage first sheath control 550 with the sheath 170, regardless of the state of the sheath stop. Alternatively, rather than a single member protruding from opposing sides of housing 520, combination stop control and sheath engagement control 556 can include two separate protrusions, acting as buttons extending from either side of housing 520, each independently performing the functions of either a stop control or a sheath engagement control.

It should be noted that although the terms "left" and "right" are used above in relation to the position of combination stop control and sheath engagement control 556, these terms are used for convenience of description only, and are not meant to be limiting. As one of skill in the art would appreciate, the described positions can be oriented other than left and right, for example "top" and "bottom", "proximal" and "distal", and the like.

Figure 6:
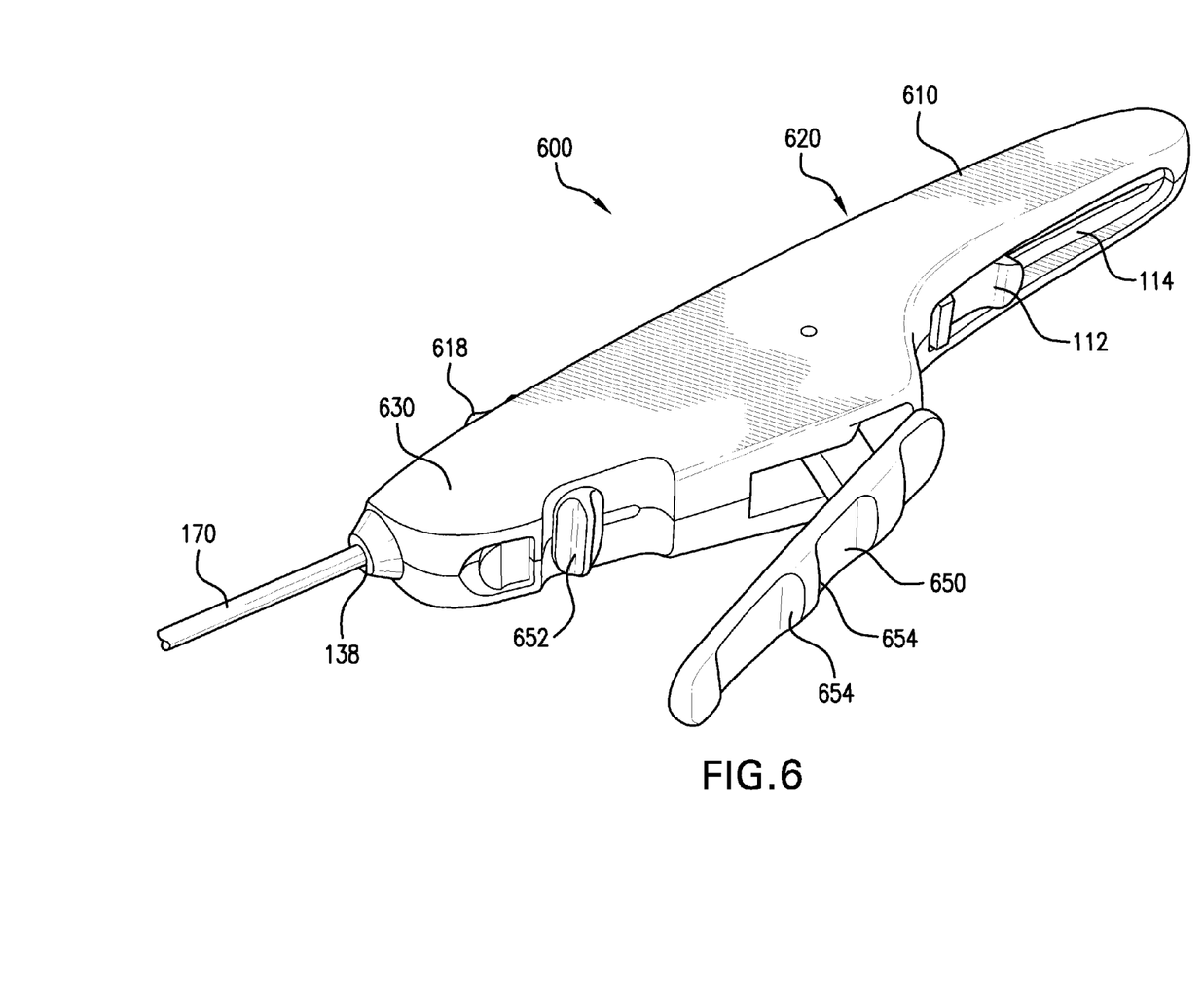
FIG. 6 is a perspective view of a delivery system according to an exemplary embodiment of the present invention.

FIG. 6 is a perspective view of a delivery system 600 according to an exemplary embodiment of the present invention. Description of elements of the exemplary embodiment depicted in FIG. 6 that are the same or operate similarly as those described above may be omitted or abbreviated.

In an exemplary embodiment of the present invention, a delivery system 600 includes a first sheath control 650 that includes a lever-based control member mounted to a housing 620 (housing 620 including a proximal portion 610 and a distal portion 630) such that the lever extends in a substantially axial direction with respect to housing 620, albeit angled thereto, depending on its state. First sheath control 650 is shown in FIG. 6 as being mounted near a midpoint of housing 620, with its lever extending in a distal direction with respect to housing 620. The lever of first sheath control 650 can be moved toward or away from housing 620. Movement of the lever in one direction will cause the sheath to move proximally with respect to the housing, thereby at least partially releasing the prosthesis. Movement of the lever in the other direction will cause the sheath to move distally with respect to the housing, thereby recapturing at least a portion of the prosthesis, if the prosthesis has not already been fully released.

Because of the location of first sheath control 650 on housing 620, as well as the mechanical advantage and precision control provided by first sheath control 650, the user can operate first sheath control 650 using his or her thumb and index finger while holding housing 620 with the palm and remaining fingers. to release or recapture the prosthesis with the fingers of the user's hand that is grasping 620, without the need to employ the user's other hand. In order to facilitate such operation, first sheath control 650 can be provided with grip enhancers 654, which, in the embodiment of FIG. 6, are grooves extending across the lever of first sheath control 650.

It should be noted that although the lever of first sheath control 650 is shown in FIG. 6 as being mounted near a midpoint of housing 620, with its lever extending in a distal direction with respect to housing 620, this configuration is exemplary, and is not meant to be limiting. As one of skill in the art would appreciate, sheath control 650 can be positioned in a variety of configurations with respect to housing 620. For example, first sheath control 650 could be mounted near a midpoint of housing 620 with its lever extending in a proximal direction with respect to housing 620, or it could be mounted near an endpoint (either proximal or distal) of housing 620 with its lever extending toward the opposing endpoint of housing 620.

Delivery system 600 can also include a sheath stop that, when engaged, limits the axial motion of sheath 170 with respect to housing 620. A stop control 652 can be actuated to disengage the sheath stop, thereby allowing axial motion of sheath 170 beyond the limits imposed when the sheath stop is engaged (e.g., allowing axial motion of sheath 170 to its full proximal position). Typically a user would operate stop control 652 to release the sheath stop once the user is certain of proper placement of the prosthesis. Thereafter, the user can operate first sheath control 650 to advance and fully release the prosthesis. As shown in FIG. 6, in an exemplary embodiment stop control 652 is a slidable control member disposed on the exterior surface of housing 620. Stop control 652 can be located on housing 620 under or proximate to the lever of first sheath control 650. This positioning facilitates easy single-handed access by a user. As described above, a user can grasp delivery system 600 with one hand such that his or her fingers wrap around housing 620 and are positioned on or proximate to the lever of first sheath control 650. In such a position, the user's fingers would be positioned proximate to stop control 652. Stop control 652 is slidable in an axial direction with respect to housing 620 between a proximal position and a distal position. Sliding stop control 652 from one position to the other disengages or engages the sheath stop. For example, sliding sheath stop control 652 from the distal position to the proximal position can cause sheath stop control 652 to disengage, at which point a user can continue to operate first sheath control 650 to move sheath 170 beyond the limits otherwise imposed by the sheath stop.

Delivery system 600 can also include a sheath engagement control 618 that is separate from second sheath control 112 and is slidably disposed on the exterior surface of housing 620. Sheath engagement control 618 can be located on a side of housing 620 opposite to that of first sheath control 650. This positioning facilitates single-handed access by a user. Sliding sheath engagement control 618 from one position to the other disengages or engages first sheath control 650 from sheath 170. For example, sliding sheath engagement control 618 from the proximal position to the distal position can cause sheath engagement control 618 to disengage first sheath control 650 with sheath 170, at which point a user can slide second sheath control 112 to control movement of sheath 170. The user can slide sheath engagement control 618 from the distal position to the proximal position in order to re-engage first sheath control 650 with sheath 170. In some exemplary embodiments, sheath engagement control 618 is spring-loaded such that it resists sliding from the proximal position to the distal position. In such an exemplary embodiment, a user who has slid sheath engagement control 618 to a distal position in order to disengage first sheath control 450 with sheath 170 need only release sheath engagement control 618 in order to allow sheath engagement control 618 to return to the proximal position and re-engage first sheath control 650 with sheath 170.

Figure 7:
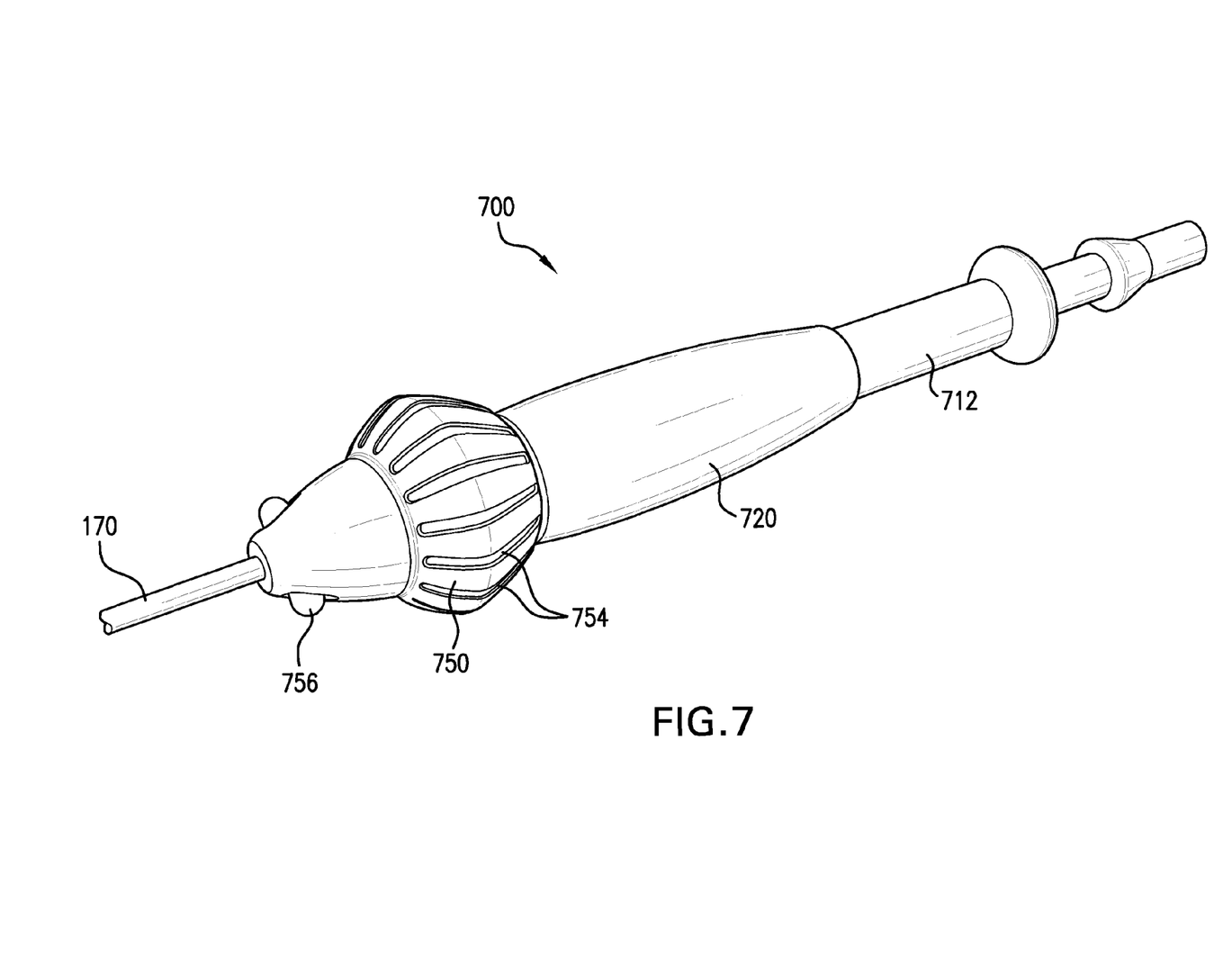
FIG. 7 is a perspective view of a delivery system according to an exemplary embodiment of the present invention.

FIG. 7 is a perspective view of a delivery system 700 according to an exemplary embodiment of the present invention. Description of elements of the exemplary embodiment depicted in FIG. 7 that are the same or operate similarly as those described above may be omitted or abbreviated.

In an exemplary embodiment of the present invention, a delivery system 700 can include a first sheath control 750 aligned coaxially with respect to a housing 720. First sheath control 750 includes gripping enhancements 754. First sheath control 720 will operate similarly to first sheath control 150, described above with reference to FIGS. 1-3. Delivery system 700 can also include a combination stop control and sheath engagement control 756 positioned near a distal end of housing 720. Such combination stop control and sheath engagement control 756 will operate similarly to combination stop control and sheath engagement control 556, described above with reference to FIG. 5.

Delivery system 700 can also include a second sheath control 712 extending longitudinally from a proximal end of housing 720. Second sheath control 712 can be fixed to sheath 170 and axially slidable with respect to housing 720. Second sheath control 712 can move proximally or distally with respect to housing 720 during operation of first sheath control 750 as a consequence of first sheath control 750 moving sheath 170. Because second sheath control 712 extends from the proximal end of housing 720, it can be viewed by a user, thereby providing to the user an indication of the extent of movement of sheath 170. As an alternative to moving sheath 170 by way of first sheath control 750, a user can choose instead to move sheath 170 by way of second sheath control 712. As the user grips housing 720, the user can position a rear portion of his or her hand on second sheath control 712, and can slide second sheath control 712 proximally or distally with respect to housing 720, thereby causing a corresponding movement of sheath 170 and at least partial release or recapture of the prosthesis.

While various exemplary embodiments of the present invention have been described above, they have been presented by way of example only, and not limitation. The elements of the exemplary embodiments presented above are not necessarily mutually exclusive, but can be interchanged to meet various needs as would be appreciated by one of skill in the art. Although the exemplary embodiments presented above allow a user to operate the delivery devices with one hand, it would be appreciated by one of skill in the art that the exemplary embodiments can also be operated with multiple hands, or with a single hand and another body part or implement.

It therefore will be apparent to one skilled in the art that various changes in form and detail can be made to the exemplary embodiments disclosed herein without departing from the spirit and scope of the present invention. The phraseology or terminology herein is used for description and not for limitation. Thus, it is intended that the present invention cover modifications and variations of this invention provided they come within the scope of the appended claims and their equivalents.

What is claimed is:

1. A delivery system for delivering a prosthesis to a location in a body, the delivery system comprising:
   a housing having a longitudinal axis, a proximal end, and a distal end;
   a sheath extending from within the housing;
   a sheath control coupled to the housing and accessible from an exterior of the housing, wherein the sheath control is operatively engaged with the sheath, and wherein a first actuation of the sheath control causes the sheath to move axially in a proximal direction with respect to the sheath control; and
   a stop control coupled to the housing and accessible from the exterior of the housing, wherein the stop control has an engaged position and a disengaged position,
   wherein, when the stop control is in the engaged position, a sheath stop allows the sheath to be moved axially in a proximal direction by the sheath control to a predetermined stop position but prevents the sheath from being moved axially in the proximal direction by the sheath control beyond the predetermined stop position,
   wherein, when the stop control is in the disengaged position, the sheath can move axially in the proximal direction beyond the predetermined stop position.

2. The delivery system of claim 1, wherein the housing comprises a proximal slot extending longitudinally through a proximal portion of the housing, and wherein a second sheath control is accessible and axially slidable within the proximal slot, the second sheath control being fixed to the sheath such that the sheath moves axially with the second sheath control.

3. The delivery system of claim 1, wherein, when the stop control is engaged, operation of the sheath control can cause the sheath to move axially in the distal direction.

4. The delivery system of claim 1, wherein the stop control remains coupled to the housing whether in the engaged position or the disengaged position.

5. The delivery system of claim 1, wherein the stop control is disposed between a proximal end and a distal end of the housing.

6. The delivery system of claim 1, wherein the stop control is disposed adjacent the sheath control such that both can be operated by a single hand of the user.

7. The delivery system of claim 1, wherein the stop control is located at a distal end of the sheath control.

8. The delivery system of claim 2, wherein the stop control is a ring located at a distal end of the sheath control.

9. The delivery system of claim 8, wherein the stop control is actuated by moving the ring in a distal direction.

10. The delivery system of claim 9, wherein actuating the stop control disengages the sheath stop.

11. The delivery system of claim 1, wherein the stop control is actuated by moving the stop control in a distal direction.

* * * * *